United States Patent
Chapoulaud et al.

(10) Patent No.: US 7,324,694 B2
(45) Date of Patent: Jan. 29, 2008

(54) FLUID SAMPLE ANALYSIS USING CLASS WEIGHTS

(75) Inventors: Eric Chapoulaud, Pasadena, CA (US); Harvey L. Kasdan, Sherman Oaks, CA (US)

(73) Assignee: International Remote Imaging Systems, Inc., Chatsworth, CA (US)

(*) Notice: Subject to any disclaimer, the term of this patent is extended or adjusted under 35 U.S.C. 154(b) by 634 days.

(21) Appl. No.: 10/850,786

(22) Filed: May 21, 2004

(65) Prior Publication Data

US 2005/0008228 A1 Jan. 13, 2005

Related U.S. Application Data

(60) Provisional application No. 60/473,176, filed on May 23, 2003.

(51) Int. Cl.
G06K 9/62 (2006.01)
(52) U.S. Cl. ............ 382/224; 377/11; 356/39; 702/21
(58) Field of Classification Search ............ 382/133, 382/170, 224, 100, 128, 227; 377/11, 13; 356/39; 702/21
See application file for complete search history.

(56) References Cited

U.S. PATENT DOCUMENTS

| | | | |
|---|---|---|---|
| 4,338,024 A | | 7/1982 | Bolz et al. |
| 4,393,466 A | | 7/1983 | Deindoerfer et al. |
| 4,612,614 A | | 9/1986 | Deindoerfer et al. |
| 4,667,335 A | | 5/1987 | Deindoerfer |
| 4,965,725 A | * | 10/1990 | Rutenberg ............ 382/224 |
| 5,703,959 A | * | 12/1997 | Asano et al. ............ 382/133 |
| 5,741,213 A | * | 4/1998 | Kouchi et al. ............ 600/310 |
| 5,822,447 A | * | 10/1998 | Kasdan ............ 382/133 |
| 6,141,624 A | | 10/2000 | Kasdan et al. |
| 6,960,756 B1 | | 11/2005 | Penumadu et al. |

(Continued)

FOREIGN PATENT DOCUMENTS

JP  5322882  12/1993

(Continued)

OTHER PUBLICATIONS

U.S. Appl. No. 10/716,589, filed Nov. 2003, Castlemen et al.

(Continued)

*Primary Examiner*—Bhavesh M Mehta
*Assistant Examiner*—Anand Bhatnagar
(74) *Attorney, Agent, or Firm*—DLA Piper US LLP (57) ABSTRACT

Most automatic particle classification methods produce errors. The invention provides a method for improving the accuracy of particle classification while shortening the amount of manual review time required from the operator. The method uses class weights, which are statistically-derived correction factors that accounts for frequency of classification errors. A first class weight and a second class weight are assigned to the first class and the second class, respectively. The number of particles in each of the first and the second classes is multiplied by the first class weight and the second class weight, respectively, to generate a corrected number of particles in each of the classes. If particles are reclassified, the class weights are recalculated in response to the reclassification. The method is usable with a complete classification where all the particles in a sample are classified, or a selective classification of a subset of the particles in the sample.

53 Claims, 3 Drawing Sheets

U.S. PATENT DOCUMENTS

2002/0031255 A1* 3/2002 Kasdan et al. ............... 382/156

OTHER PUBLICATIONS

Castleman, Kenneth R., "Pattern Recognition: Classification And Estimation," pp. 538-545, Digital Image Processing (1996 by Prentice-Hall, Inc.).

PCT Search Report and PCT Written Opinion mailed on Jan. 10, 2006 corresponding to the related PCT Patent Application No. US04/16158.

* cited by examiner

FLUID SAMPLE ANALYSIS USING CLASS WEIGHTS

RELATED APPLICATION

This application claims the benefit of U.S. Provisional Application Ser. No. 60/473,176 filed on May 23, 2003, pursuant to 35 U.S.C. § 119(e). The content of the Provisional Application Ser. No. 60/473,176 is hereby incorporated by reference in its entirety.

FIELD OF THE INVENTION

The present invention relates generally to methods and systems for analyzing particles in a sample and more particularly for determining the concentration of particles in the sample.

BACKGROUND OF THE INVENTION

Methods and apparatuses for processing images of particles in a fluid sample are well known. For example, U.S. Pat. Nos. 4,667,335 and 4,612,614 describe apparatuses having a software program that determines various characteristics of particles (e.g., biological particles) by using an imaging signal. The apparatuses disclosed in these references can automatically—i.e., without human intervention—determine characteristics such as color, size, and brightness of particles in a fluid sample. Moreover, based on the determined characteristics, these apparatuses can categorize each particle into one of many classes and calculate the concentration of each particle type (i.e., particle class). This automatic sample analysis and concentration determination process is referred to as Auto-Particle Recognition (APR).

For practical reasons, a limit is usually imposed on the amount of sample that is analyzed. In one conventional apparatus, the sample is analyzed one portion at a time such that a first portion is analyzed, the number of particles in that portion is counted, a next portion is then analyzed, the number of particles in that portion is added to the total count, etc. This portion-by-portion particle counting process continues until a maximum time period passes, maximum total sample volume is reached, or a maximum number of particles is counted.

The classification and calculation results are typically displayed in the manner similar to that disclosed in U.S. Pat. No. 5,822,447. Namely, a plurality of optical frames are taken, wherein each frame is a picture of a portion of the sample. Preferably, the frames represent different portions of the sample. A frame is made of one or more "patches" of images, with each patch containing at least one particle image. The patches are classified into one of a plurality of classes based on the images they contain, and the classes are usually characterized by one or more visually discernible characteristics. In some embodiments, if a patch contains more than one discernable particle image, the particle images could be classified separately. In other embodiments, the image of the more predominant particle is used to classify the patch. After the classification, the concentrations of each class of particles are determined.

The patches extracted from the frames are displayed on a graphical user interface (e.g., a computer monitor), preferably in an ordered array by classification. The number of particles within each class, or any parameter derived therefrom (e.g., a percentage of the total number of particles), may be displayed. The APR process determines the concentration of each particle type (i.e., particle class) based on this classification. Then, an operator manually reviews the APR classification results and corrects any errors. During the manual review process, the operator may pull a misclassified particle out of one class and add it to another class.

There are a few different modes of particle classification, and the mode that is used affects the way in which the operator conducts the manual review. In the complete classification mode, all the particles in a sample are individually classified. The manual review process that follows the complete classification is a Full Edit mode of review whereby the operator manually checks each individual classified particle image to ensure proper classification. During the Full Edit process, the operator reclassifies misclassified particle images into the proper particle class. While the Full Edit mode is advantageous in that every resulting classification is one that has been manually "approved" by the operator and therefore highly likely to be accurate, it is very time consuming for the operator. Thus, the complete particle classification and the Full Edit mode are preferably used with a sample that contains a relatively small number of particles (e.g., less than 1000 particles).

In the partial classification mode, which is described in more detail in U.S. Pat. No. 6,141,624, the operator reviews only a subset of the particle images. Of the I number of particles in the sample, at most $N_{MAX}$ particles are selected for operator review and classified ($N_{MAX}$<I). Since the operator does not review all the I particles, the average review time required of the operator can be significantly reduced relative to the complete classification mode. The manual review and edit process that follows the partial classification is sometimes referred to as being in the Abbreviated Edit mode. The partial classification and Abbreviated Edit mode are ideal for larger samples containing thousands and even tens of thousands of particles.

The complete classification yields an accurate result but demands a lot of time from the operator. The partial classification demands less time from the operator but the accuracy may be compromised. A method that will help the operator save time in the complete classification mode and improve the accuracy of the partial classification mode is desired.

SUMMARY OF THE INVENTION

The invention provides a method and system for improving the accuracy of particle concentrations determined by a fluid sample analyzer while shortening the amount of review time required of the operator.

In one aspect, the invention is a method of analyzing a fluid sample containing I number of particles. The method entails classifying N number of particles into one of a first class, a second class, and an artifact class, wherein the classifying into the first and second classes is performed based upon the particles meeting first and second predefined class criteria, respectively, and wherein the classifying into the artifact class is performed based upon a failure of the particles to meet either of the first and second predefined class criteria. A first class weight and a second class weight are determined based upon known prior mis-classifications of particles for the first and second classes, respectively. The number of the particles classified into the first class is multiplied by the first class weight to generate a corrected number of particles classified into the first class, and the number of the particles classified into the second class is multiplied by the second class weight to generate a corrected number of particles classified into the second class.

In another aspect, the invention is a set of computer-readable instructions for analyzing a sample that contains I particles. The instructions include instructions for classifying N number of particles into one of a first class, a second class, and an artifact class. The criteria for the first class and the second class are predefined. A particle that is not identified as belonging to either the first class or the second class is classified into the artifact class. The computer-readable instructions also include instructions for determining a first class weight for the first class and a second class weight for the second class. The computer-readable instructions further include instructions for multiplying a number of the particles that are classified into the first class by the first class weight to generate a corrected number of particles classified into the first class, and instructions for multiplying a number of the particles classified into the second class by the second class weight to generate a corrected number of particles classified into the second class.

In yet another aspect, the invention is a device for analyzing a fluid sample that embodies the above computer-readable program.

DETAILED DESCRIPTION OF THE PREFERRED EMBODIMENTS

Embodiments of the invention are described herein in the context of a urinalysis system, and particularly to an in-vitro urinalysis diagnostic device that generally utilizes the technologies disclosed in U.S. Pat. Nos. 4,338,024 and 4,393,466. However, it is to be understood that the embodiments provided herein are just preferred embodiments, and the scope of the invention is not limited to the applications or the embodiments disclosed herein.

A "particle," as used herein, is any substance that may be carried in a fluid sample, including but not limited to a cell. "Misclassification," as used herein, includes identifying a particle as something that belongs to a class that is different from the actual class it belongs to. "Reclassification" of a particle is changing the class of a particle from one class to another, and includes moving a particle between an artifact class and a class with a predefined set of criteria.

The invention includes a systematic method of correcting the classification errors so that the particle concentrations can be determined with a reasonable level of accuracy while demanding less time from the operator. If the operator chooses to perform a manual review, the concentration results calculated by the method of the invention will help the operator perform the review more efficiently by providing a reasonably accurate guideline as to what the end result will look like.

The method of the invention assigns a class weight (CW) to each particle class. The class weight is a unit-less parameter obtained from statistical evaluation of the correlation between average results of the preliminary classification and perfect, error-free results. The class weight, in effect, is a multiplier that compensates for the fact that the preliminary classification commits errors at a certain frequency (e.g., one misclassification out of every x particles). The class weight is usually different for each particle class. All particles belonging to a particular particle class share the same class weight value.

In an exemplary sample that contains red blood cells and white blood cells, there are three particle classes: a red blood cell class (R), a white blood cell class (W), and an artifact class. An artifact class is a "catch-all" type class that is used for particles that are not clearly identified as belonging to one of the predefined classes. If it is known from prior runs and edits that only 50% of all the red blood cells are correctly classified as red blood cells, and only 30% of all the white blood cells are classified as white blood cells on the average, the class weights for red blood cells and white blood cells, respectively, would be 2 and 3.3. If the number of particles that are in class R is multiplied by the class weight for red blood cells (2), and the number of particles in class W is multiplied by the class weight for white blood cells (3.3), the resulting numbers will approximate the correct numbers of red blood cells and white blood cells in the sample. The class weight takes into account the possibility that a red blood cell may have erroneously been classified as a white blood cell, and vice versa. In addition, the class weight also accounts for the fact that statistically determined fractions of all the red blood cells and all the white blood cells are preliminarily classified in the artifact class.

One way of determining the class weight for a particle class is to use a look up curve. A look up curve can be established that correlates the results obtained by the preliminary classification process (e.g., APR) and the results after a more complete review and correction by a human operator. The inverse of this look up curve equals the class weight. A regression analysis using a linear model could be used to approximate the class weight. A class weight of 1 means that the APR process and the human-corrected process produce the same results (i.e., the APR result is error free). A class weight higher than 1 indicates that less than all the particles of the class are properly classified in that class by the initial classification method. Thus, the initial class weights are usually 1 or higher, with artifacts having a class weight of 1.

If a class weight is determined based on statistical evaluation and subsequently there is a reclassification by the operator, the class weight (i.e., the class weight before reclassification) is recalculated to reflect the reclassification. Since each class is associated with a particular class weight and the different classes usually have different class weights, an operator's re-classifying a particle affects the particle concentrations for a few different classes. For example, if the concentration of red blood cells is determined to be $C_{R,\ Old}$ and the concentration of white blood cells is determined to be $C_{W,\ Old}$ based on the preliminary classification, moving a misclassified particle from class W to class R will affect the concentrations $C_{R,\ New}$ and $C_{W,\ New}$.

Once the number of particles in each class is determined by using the class weight, concentrations are calculated. Details on how to calculate the concentration are provided below. As used herein, I represents the total number of particles in a sample.

Figure 1:
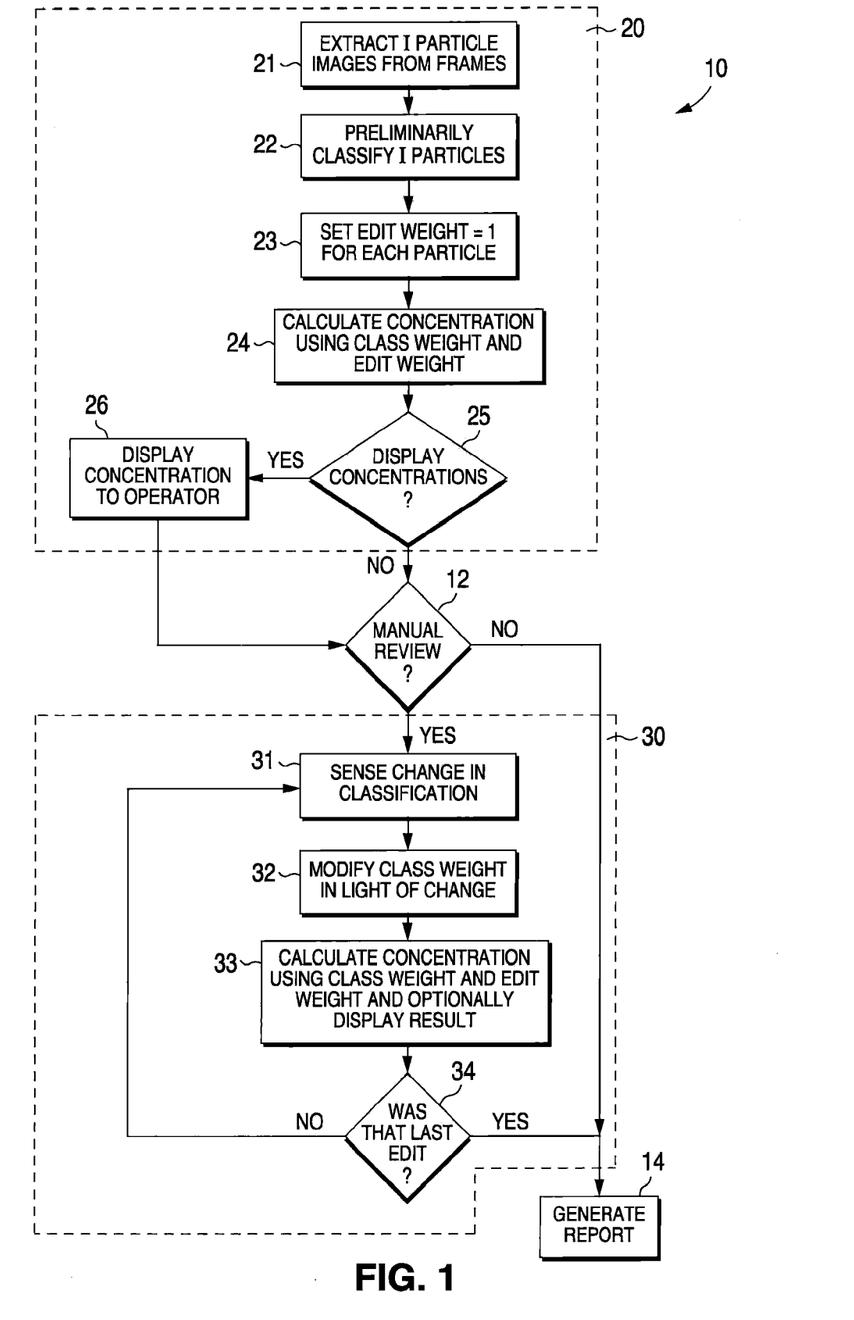
FIG. 1 is a flowchart of a complete classification process in accordance with a first embodiment of the invention.

FIG. 1 is a flowchart depicting a complete classification process 10 in accordance with an embodiment of the invention. The complete classification process 10 includes a preliminary determination process 20 and a full edit process 30. As described above, frames (still pictures) of the sample are taken and particle images are extracted from the frames (step 21). Then, a preliminary classification is performed whereby the particle images are placed into one of a predefined set of classes (step 22). During this preliminary classification process, particles that are not identified as belonging to one of the predefined set of classes with a pre-selected level of certainty are classified in the artifact class. At the end of the preliminary classification process, all I particles in the sample are classified. This preliminary classification may be performed through an automatic process such as the APR process, which is a neural net based process described in U.S. patent application Ser. No. 09/841,941 filed on Apr. 24, 2001 and U.S. patent application Ser. No. 10/716,589 filed on Nov. 18, 2003, both of which are incorporated herein by reference. During preliminary classification, the system that runs the process 10 may maintain a record of which frame each particle image was extracted from. Although the APR process is an automatic process, preliminary classification may be performed using any well known classification method and does not have to be a 100% automatic process.

After the preliminary classification, the edit weights are determined for the particles (step 23). In the case of the complete classification process 10 where all I particles are classified, the edit weight for each particle is 1 because each particle represents itself. After the edit weights are determined, the preliminary concentrations are calculated (step 24). The concentration for a class of particles is typically calculated by multiplying the number of particles in the class (i.e., the sum of the edit weights of particles in the class wherein each edit weight=1) with the class weight and dividing the product by the sample volume. The concentrations may be calculated in any desired unit, such as number of particles per volume or the percentage of a particular class of particles out of the total number of particles. If the operator chooses to see the concentrations based on the preliminary classification (step 25), the concentrations are displayed to the operator (step 26).

The operator may choose to accept the calculated concentration results without a detailed review of the classifications, or conduct a manual review (step 12). If the operator chooses to release the results without further review, the results are compiled into a report (step 14). On the other hand, if the operator chooses to review the results, the full edit process 30 begins.

During the full edit process 30, the operator may reclassify particles or simply "approve" the preliminary classification on a particle-by-particle basis. The system senses whether a reclassification is made by moving a particle from one class to another (step 31). When a change is sensed, a class weight modification process is triggered whereby the class weight is modified to reflect the particle reclassification (step 32). The class weight is adjusted according to the following equation:

$$CW_{New}=[(N-N_{Moved}) \cdot CW_{Old}+N_{Moved}]/N \quad (1)$$

wherein $CW_{New}$=new class weight after the adjustment;
$CW_{Old}$=old class weight before the adjustment;
N=total number of particles that are classified (including artifacts); and
$N_{Moved}$=effective number of particles that are reclassified.

When the operator approves a preliminary classification result without making any edits, the class weight modification process is not triggered. Preferably, the class weight is modified in response to every change the operator makes, so that the change in concentration due to a single move will not be dramatic. If a particle is moved from class A to class B and then back to class A, $N_{Moved}$ is incremented and then decremented to cancel out the effect of the moves. Also, if a particle is reclassified a number of times, only the first and the last classifications affect the class weight regardless of the steps in between. For example, if a particle is moved from class A to class B, then from class B to class C, and then from class C to class D, the ultimate effect on the class weight is the same as if the particle had been moved from class A to class D in a single move.

After the operator completes the edit process, the system automatically recalculates the concentrations to reflect the changes made by the operator (step 33), using the following equation:

$$C_{CLASS\ A}=(CW_{A,New} \cdot \Sigma_{(Class\ A)}EW)/REF \quad (2)$$

where REF is the Run Equivalency Factor (i.e., the volume of the sample or the total number of the particles that were classified, depending on the desired units of concentration). EW is the edit weight for a particle (defined in more detail below), and $\Sigma_{(Class\ A)}EW$ is the sum of all the edit weights of the particles in Class A. In the case of complete classification, where the edit weight of each particle is 1, $\Sigma_{(Class\ A)}EW$ is the same as the current number of particles in Class A (i.e., after the most recent reclassification). Depending on the embodiment, the recalculated concentration may be displayed to the operator.

Steps 31, 32, and 33 are repeated until there are no more changes to be made (step 34), at which point the reviewed results are incorporated into a report (step 14). When asked if more changes are desired in step 34, the operator may make further changes to the same particle that was already reclassified before, or reclassify a new particle. Eventually, when the operator is satisfied with the classification, the full edit process 30 ends. Theoretically, the only classification error that appears in the report 14 should be from human error committed by the operator. If the operator were to continue to review and edit all the particle images captured from the sample, the class weights for all the different particle classes should converge to 1.

Figure 2:
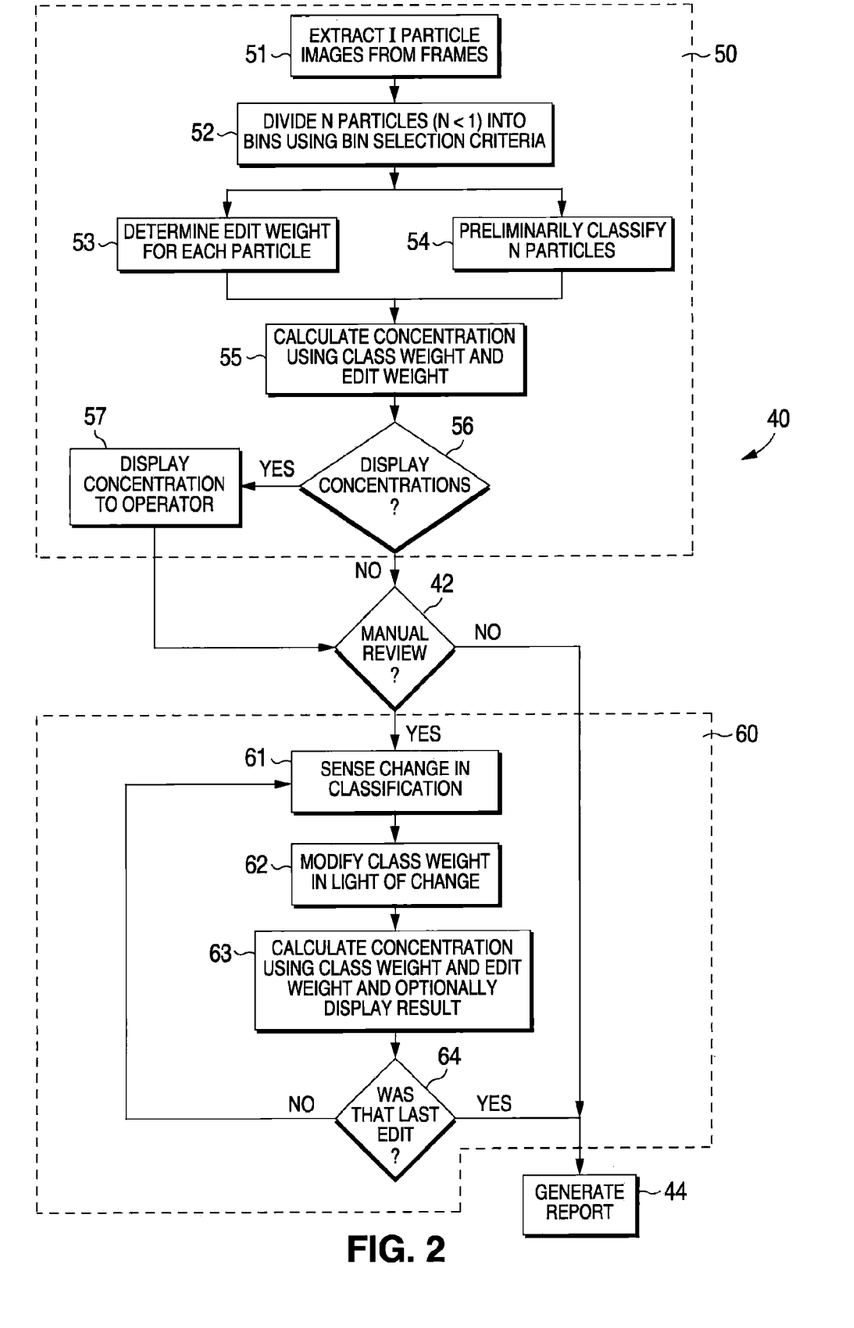
FIG. 2 is a flowchart of a partial classification process in accordance with a second embodiment of the invention.

FIG. 2 is a flowchart depicting a first partial classification process 40 in accordance with another embodiment of the invention. The first partial classification process 40 includes a preliminary classification process 50 and an abbreviated edit process 60. Similarly to the complete classification process 10, the preliminary classification process 50 starts with extraction of particle images from the frames (step 51). The extracted particle images are then divided among a certain number of Bins (step 52). Unlike in the complete classification process of FIG. 1, only N of the I particles in the sample are placed in the Bins (N<I) and only the particles that are placed in the Bins are reviewed by the operator. The particles that are placed in the Bins are, in effect, "selected" for operator review and the remaining particles are skipped and/or discarded.

The N particles that are classified may not be the first N particles in the sample because classifying the first N particles could result in classification of only the particles that exist in high concentration and failure to classify any of the particles that exist in low concentrations. The method of sampling N particles into a number of Bins is disclosed in detail in U.S. Pat. No. 6,141,624, which is incorporated by reference herein.

In an exemplary embodiment, there are three Bins: Bin A, Bin B, and Bin C, wherein each Bin is defined by a particle size range. The number of Bins and the criteria for the Bins may be determined by trial and error or some type of iterative procedure. Whatever the criteria may be, however, the Bins must be mutually exclusive and cover the entire domain of observed particles. For example, Bins A, B, and C may each hold small, medium, and large particle sizes, respectively, with size ranges assigned as follows:

Class A: particles having an image size between 0 and $S_A$ pixels (e.g., 69 pixels), Class B: particles having an image size between $(S_A+1)$ to $S_B$ pixels (e.g. 109 pixels), and Class C: particles having an image size larger than $(S_B+1)$ pixels, wherein the pixels refer to pixels of the particle images that were extracted in step 51. Depending on the application, any visually discernable characteristic of the particles (e.g. average particle brightness, color, shape, etc.) could be used instead of particle size as a selection criteria for the Bins. As used herein, particles are "selected" if they are placed into one of the Bins.

The first partial classification process 40 uses various parameters to ensure that the subgroup of particles that are classified reflect the particle mix of the total sample as closely as possible. These parameters include a maximum number of selected particles ($N_{MAX}$) and maximum Bin capacities ($MAX_{BIN\ A}$, $MAX_{BIN\ B}$, $MAX_{BIN\ C}$). $N_{MAX}$ is the maximum number of particles that may be selected from one sample, and maximum Bin capacities ($MAX_{BIN\ A}$, $MAX_{BIN\ B}$, $MAX_{BIN\ C}$) are numbers that are assigned to each of the Bins to limit the number of particles each Bin can hold. In the preferred embodiment, the system sequentially goes through the particle images (e.g. in the order that they were acquired) and places the particle images according to the particle Bin criteria until either $N_{MAX}$ has been reached or all particles have been examined (i.e., if $I<N_{MAX}$). If the maximum Bin capacity $MAX_{BIN}$ is reached for any of the Bins, no more particles are placed into the particular Bin even if they meet the criteria for the particular Bin. For example, particles that belong to Bin A are skipped and not placed into any Bin if Bin A has reached $MAX_{BIN\ A}$. While none of the maximum Bin capacities is greater than $N_{MAX}$, the sum of all the maximum Bin capacities is greater than $N_{MAX}$.

In an exemplary embodiment, each of the maximum class sizes $MAX_{BIN\ A}$, $MAX_{BIN\ B}$, and $MAX_{BIN\ C}$ is 500 particles and $N_{MAX}$ is 750 particles. If the sample contains a high concentration of particle type A, medium concentration of particle type B, and a low concentration of particle type C, Bin A will reach its maximum capacity before the other bins. At the time $MAX_{BIN\ A}$ is reached (i.e., 500 particles are in it), there may be 100 particles in Bin B and 20 particles in Bin C. Once $MAX_{BIN\ A}$ is reached, particle selection into Bin A stops and the sample volume at which the last particle was added to Bin A is noted. Sampling continues into the other Bins until $N_{MAX}$ is reached. If either Bin B or Bin C reaches its maximum capacity before $N_{MAX}$ is reached, no more particles are placed into that Bin. Particles that are determined to be type-A are skipped if Bin A is already full, and the operator does not review them. Once $N_{MAX}$ is reached, the partial classification process 50 stops.

The division of particles into Bins is used for edit weight determination (step 53). A particle edit weight (EW) is assigned to each Bin and all the particles in a Bin have the same edit weight. The edit weight is used to calculate the concentration for each class of particles, for example according to Equation (2) above. There are four possible scenarios for edit weight calculations:

1. If $N_{MAX}$ has been reached for the sample during the above described selection process, but no bin is full, then EW=File Volume Ratio (FVR) for all the selected particle images, where FVR is calculated by dividing the number of captured image frames by the number of the last frame at which $N_{MAX}$ was reached. For example, suppose the Bin selection process stopped with 400, 300, and 50 particles in Bin A, Bin B, and Bin C, respectively, where $N_{MAX}$ is 750. Suppose also that $N_{MAX}$ was reached after 150 frames were reviewed, and that the entire sample contains 400 frames. The FVR for the particles in this example would be 400/150=2.67, indicating that each particle in this example represents 2.67 particles of the same particle type.

2. If $N_{MAX}$ for the sample was not reached, but the Bin Maximum Number ($MAX_{BIN}$) has been reached for any of the Bins, then EW=Bin Volume Ratio (BVR) for the particle images in those Bins, where BVR for each Bin is calculated by dividing the number of captured image frames by the number of the last frame at which $MAX_{BIN}$ was reached for that Bin. So, for example, if 500 type-A particles are in Bin A, particle placement into Bin A stopped at the 100th frame, and the total sample volume contains 400 frames, the edit weight is 400/100=4. In this example, every particle A that is captured stands for 4 type-A particles.

3. If both $N_{MAX}$ and $MAX_{BIN}$ are reached, then the EW of particles in the Bin whose $MAX_{BIN}$ is reached is calculated with the BVR. On the other hand, the EWs of particles in the Bins that are less than full are calculated with the FVR.

4. If $I<N_{MAX}$ and all the particles in the sample are placed into the Bins without reaching either $N_{MAX}$ or a $MAX_{BIN}$, EW=1.

The N particles that are selected into the Bins are subjected to the preliminary classification process according to the visual criteria for each class (step 54). Usually, some of the N particles are classified into an artifact class because they cannot be clearly identified as belonging to one of the predefined classes. After the partial classification process, the concentrations are calculated using the class weight and the edit weight (step 55). The concentration of a particle class is the sum of the edit weights of the particles in the class multiplied by the class weight and divided by the sample volume or total number of particles I to obtain the concentration. If the operator chooses to see the concentrations (step 56), the resulting concentration is displayed to the operator (step 57), who then decides whether to manually review the preliminary classification (step 42).

If the operator chooses not to conduct a manual review, the concentrations determined in step 55 are incorporated into the report 44. On the other hand, if the operator chooses to conduct a manual review, the abbreviated edit process 60 begins.

The operator makes changes or approves a preliminary classification on a particle-by-particle basis. The system senses the operator action (step 61) so that each time a reclassification is made, the class weight is modified in response to the reclassification (step 62). By updating the class weight in response to each edit, clinically accurate concentrations for all particle classes are provided throughout the editing process as well as after the editing process is completed. The class weight is modified using Equation (1) provided above.

Then, using the new class weight, the concentrations are recalculated (step 63). The concentrations are recalculated using Equation (2) provided above, except that unlike in the case of full edit process, the edit weight of a particle (EW) is not unity in the case of partial classification. As long as there is at least one particle that is skipped for every particle of the same type that is classified, the edit weight will be greater than 1. The same edit weight applies to all the particles in each Bin, and subsequent reclassification does not affect the edit weight for a given particle. Each newly calculated concentration may be presented to the operator. By updating the concentration with each change, the operator sees small incremental changes rather than a dramatic change in concentration.

If there are no more edits to be made (step 64), the current results are incorporated into the report 44. On the other hand, if the operator wishes to reclassify any of the new or previously reclassified particles, the reclassification is made and the process loops back to step 61.

Figure 3:
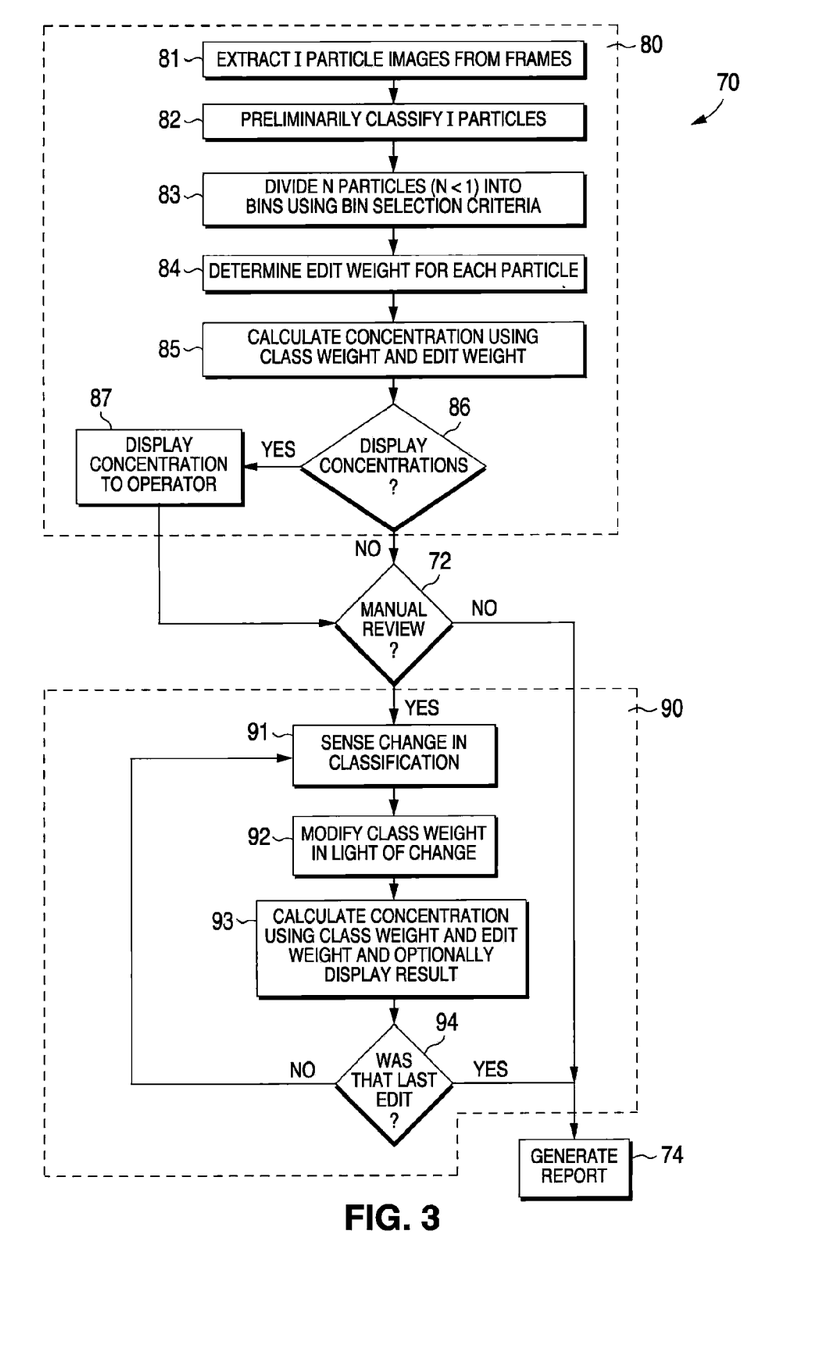
FIG. 3 is a flowchart of a partial classification process in accordance with a third embodiment of the invention.

FIG. 3 is a flowchart depicting a second partial classification process 70 in accordance with yet another embodiment of the invention. Unlike in the first partial classification process 40, the preliminary classification is performed before the Bin selection process in the second partial classification process 70. The second partial classification process 70 may yield results that are different from the first partial classification process 40 because, the preliminary classification that is performed before the Bin selection may affect the Bin selection results. For example, particle classification or some trait associated with a class of particles may be used as part of the Bins selection criteria.

The second partial classification process 70 includes a preliminary classification process 80 and an abbreviated edit process 90. In the preliminary classification process 80, I particle images are extracted from frames (step 81), and all of the I particle images are preliminarily classified (step 82). After each particle is associated with a class, N of the I particle images are divided into Bins using predefined Bin selection criteria (step 83). The edit weights are determined for each particle (step 84), and the concentrations are calculated using the class weight and edit weight (step 85). If the operator wishes to see the concentrations (step 86), they are displayed to the operator (step 87).

The abbreviated edit process 90 is substantially similar to the abbreviated edit process 60 of the first partial classification process 40.

The following examples illustrate the effects of reclassification on particle concentrations.

EXAMPLE 1

This example illustrates the effect of reclassification on class weight and concentration. Suppose there is a three-class system having class R, class W, class C, and an artifact class. Suppose also that $CW_R=2$, $CW_W=1.5$, and $CW_C=4$. After the APR process, there are 40 particles in class R, 20 particles in class W, 5 particles in class C, and 50 particles in the artifact class per unit volume. The total number of particles (N) is 115. The initial concentrations should be as follows:

$$C_R = 2 \times 40 = 80 \text{ particles/volume}$$

$$C_W = 1.5 \times 20 = 30 \text{ particles/volume}$$

$$C_C = 4 \times 5 = 20 \text{ particles/volume.}$$

Assuming REF=1 and using Equation (1) and Equation (2) provided above:

$$C_R = CW_{R,New} \times \Sigma_{(Class)EW} = \{[2(115-3)+3]/115\} \times 41 = 80.93 \text{ particles/volume}$$

$$C_W = CW_{W,New} \times \Sigma_{(Class)EW} = \{[1.5(115-3)+3]/115\} \times 19 = 28.25 \text{ particles/volume}$$

$$C_C = CW_{C,New} \times \Sigma_{(Class)EW} = \{[4(115-3)+3]/115\} \times 5 = 19.6 \text{ particles/volume}$$

The reclassification results show that there is no dramatic change in concentration by moving one particle (overall result of the three moves being reclassifying a W to R). It should be noted that although class C was not directly affected by the reclassification, its concentration was affected.

EXAMPLE 2

This example illustrates the effect of classifying particles that were originally classified in the artifact class. The same initial conditions are assumed as in Example 1. During reclassification, five artifacts are moved to class C. Again assuming REF=1 and using Equations (1) and (2), the new concentrations are as follows:

$$C_R = CW_{R,New} \times \Sigma_{(Class)EW} = \{[2(115-5)+5]/115\} \times 40 = 78.26 \text{ particles/volume}$$

$$C_W = CW_{W,New} \times \Sigma_{(Class)EW} = \{[1.5(115-5)+5]/115\} \times 20 = 29.56 \text{ particles/volume}$$

$$C_C = CW_{C,New} \times \Sigma_{(Class)EW} = \{[4(115-5)+5]/115\} \times 10 = 38.7 \text{ particles/volume}$$

Moving five artifacts into class C almost doubled the concentration of class C.

An Alternative Method

Now, an alternative method for recalculating the class weight and concentration will be presented. The preliminary classification steps are the same for this alternative method as for the method described above.

In this alternative method, decreasing of the class weight is preferably performed using the following equation:

$$\begin{cases} CW^n = 1 |_{CW=1} \\ CW^n = \text{Maximum} \left(1, \dfrac{\left[\sum_{\{Class\}} EW\right] - EW_{Moved\ Particle}}{\sum_{\{Class\}} EW} CW_{Old}\right) \end{cases} \quad (3)$$

wherein $CW^n$=the newly calculated class weight after reclassification (similar to $CW_{New}$ in the first method). According to Equation (3), the class weight is left at 1 if it was already 1 before the reclassification. Otherwise, the class' new class weight ($CW^n$) is the product of its old class weight ($CW_{Old}$) and a coefficient, which is the sum of the class's particle edit weights ($\Sigma_{(Class)}$ EW) after the move, minus the edit weight of the moved particle, divided by the sum of the class's particle edit weights ($\Sigma_{(Class)}$ EW) after the move. If the product of the coefficient and $CW_{Old}$ is less than 1, then the new class weight is 1 (1 is the lowest possible value of $CW^n$ for Equation (3)).

Increasing the class weight is preferably performed using the following equation:

$$\begin{cases} CW^n = 1 \mid_{CW=1} \\ CW^n = \dfrac{\left[\sum_{\{Class\}} EW\right] + EW_{moved\ Particle}}{\sum_{\{Class\}} EW} CW_{Old} \end{cases} \quad (4)$$

Again, if the Class Weight was already 1 before the move, it is left at 1. Otherwise, the class' new Class Weight ($CW^n$) is the product of its old Class Weight ($CW_{Old}$) and a coefficient, which is the sum of the class's particle edit weights (EW) after the move, plus the edit weight of the particle moved into the class, divided by the sum of the class's particle edit weights (EW) after the move.

When a particle is reclassified by the operator, the particle concentration for each class affected by the move is recalculated using the following equation:

$$C_{CLASS\ A} = (CW^n \cdot \Sigma_{(Class\ A)EW})/REF \quad (5)$$

Equation (5) is similar to Equation (2) except that $CW^n$, which is calculated using Equations (3) and (4), is used instead of $CW_{New}$, which is obtained by Equation (1). In the case of complete classification, $\Sigma_{(Class)}EW$ is equal to the number of particles in Class A after the most recent reclassification, since the edit weight of each particle is 1. In the case of partial reclassification, however, the value of $\Sigma_{(Class)}EW$ is typically greater than 1, since at least some of the particles represent more than one particle.

The class weight CW for each particle class may change depending upon the type of edit made by the operator. For example, suppose that the operator reclassifies a particle image by moving it from Class A to Class B. The following changes to class weight CW are made at the time the move is made depending upon the particle classes affected by the move:

i) If Class A has a class weight (CW) of 1 (i.e. an artifact class), and Class B has a class weight (CW) strictly superior to 1 (i.e. not an artifact class), then:
   the calculated concentration of Class A will decrease per Equation 5, and the class weight CW of Class A will stay the same, and
   the calculated concentration of Class B will stay the same per Equation 5 by decreasing the class weight (CW) of Class B preferably using Equation 3.

ii) If Class A has a class weight (CW) strictly superior to 1 (i.e. not an artifact class), and Class B has a class weight (CW) of 1 (i.e. an artifact class), then:
   the calculated concentration of Class A will stay the same per Equation 5 by increasing the class weight (CW) of Class A preferably using Equation 4, and
   the calculated concentration of Class B will increase per Equation 5, and the class weight CW of Class B will stay the same.

iii) If Class A has a class weight (CW) strictly superior to 1 (i.e. not an artifact class), and Class B has a class weight (CW) strictly superior to 1 (i.e. not an artifact class), then:
   the calculated concentration of Class A will decrease per Equation 5, and the class weight CW of Class A will stay the same, and
   the calculated concentration of Class B will increase per Equation 5 and the class weight CW of Class B will stay the same.

iv) If Class A has a class weight (CW) of 1 (i.e. an artifact class), and Class B has a class weight (CW) of 1 (i.e. an artifact class), then:
   the calculated concentration of Class A will decrease per Equation 5, and the class weight CW of Class A will stay the same, and
   the calculated concentration of Class B will increase per Equation 5, and the class weight CW of Class B will stay the same.

v) If Class B is created (by moving the particle into it), then class weight CW for Class B is initially assigned a class weight value equal to the initial class weight that would have been used had there been a particle in the class, as discussed above.

vi) If Class A is emptied (by removing the only particle in it), then Class A will have no defined class weight CW. Should a particle image subsequently be moved back into Class A, then it is initially assigned a class weight value equal to $CW_{Old}$ (i.e. the last class weight before the class was emptied) as discussed above.

vii) Once an operator moves any particle image from Class A (its original APR determined class) to Class B as described above, and then subsequently moves that same particle image from Class B to Class C, then:
   Apply the above rules to move the particle image from Class B to Class A, and then
   Apply the above rules to move the particle image from Class A to Class C.

EXAMPLE 3

This example illustrates the effect of reclassification on class weight and concentration using Equations (3), (4), and (5). Suppose the same initial conditions as that provided above in Example 1. If the operator reclassification moves two of the particles that were originally in class W to class R and one of the particles in class R to class W (total number of reclassified particles=3), the class weights do not change, per situation iii) described above. Using the same class weights and REF=1, the concentrations calculated with Equation (5) are as follows:

$C_R = 2 \times 41 = 82$ particles/volume $C_W = 1.5 \times 19 = 28.5$ particles/volume $C_C = 4 \times 5 = 20$ particles/volume

EXAMPLE 4

Suppose the same initial condition as that described in Examples 1 and 3. Suppose also that one particle is now moved from the artifact class to class C. The class weight for the artifact class remains the same but the class weight of class C decreases per Equation (3), as described in situation i) above. Thus, the concentrations are as follows:

$C_R = 2 \times 40 = 80$ particles/volume $C_W = 1.5 \times 20 = 30$ particles/volume $C_C = (5/6 \times 4) \times 6 = 20$ particles/volume.

This example demonstrates that moving one particle from the artifact class to class C does not affect the concentration of Class C when using the alternative method.

EXAMPLE 5

Suppose the same initial conditions as in Example 4 except that this time, 20 particles are moved from the artifact class to class C. The concentrations will now be as follows:

$C_R = 2 \times 40 = 80$ particles/volume $C_W = 1.5 \times 20 = 30$ particles/volume $C_C = \text{Maximum } [1, 5/25 \times 4] \times 25 = \text{Maximum } [1, 0.8] \times 25 = 25$ particles/volume.

When 20 particles are moved from the artifact class to class C, the concentration of class C is changed.

The application of class weights may be implemented in a program as a set of computer-readable instructions in a machine that executes the APR process. Similarly, the modification of class weights and calculation of concentrations may be implemented in a program to minimize human involvement. Although FIG. 1 and FIG. 2 illustrate complete classification and partial classification separately, this is done for clarity of explanation and the same system may be used to perform both types of classifications. Preferably, the system has a local switch so the operator can toggle between the Full Edit mode and Abbreviated Edit mode.

Although preferred embodiments of the present invention have been described in detail hereinabove, it should be clearly understood that many variations and/or modifications of the basic inventive concepts herein taught which may appear to those skilled in the present art will still fall within the spirit and scope of the present invention.

What is claimed is:

1. A method of analyzing a fluid sample containing I number of particles, the method comprising:
   classifying N number of particles into one of a first class, a second class, and an artifact class, wherein the classifying into the first and second classes is performed based upon the particles meeting first and second predefined class criteria, respectively, and wherein the classifying into the artifact class is performed based upon a failure of the particles to meet either of the first and second predefined class criteria;
   determining first and second class weights based upon known prior mis-classifications of particles for the first and second classes;
   multiplying a number of the particles classified into the first class by the first class weight to generate a corrected number of particles classified into the first class; and
   multiplying a number of the particles classified into the second class by the second class weight to generate a corrected number of particles classified into the second class.

2. The method of claim 1 further comprising assigning a class weight of one to particles in the artifact class.

3. The method of claim 1 further comprising:
   determining an edit weight that for each of the particles; and
   calculating a concentration of the first class particles and the second class particles by using the class weight and the edit weight.

4. The method of claim 3, wherein N is less than or equal to I and determining the edit weight comprises a bin selection process that includes:
   setting up a first bin for first-type particles and a second bin for second-type particles, wherein the first-type particles and the second-type particles are defined by a set of mutually exclusive bin selection criteria;
   selecting a maximum particle number ($N_{MAX}$) to be checked for placement into the first bin and the second bin;
   setting a maximum first bin capacity $MAX_{BIN\ 1}$ for the first bin and a maximum second bin capacity $MAX_{BIN\ 2}$ for the second bin; and
   placing the first-type particles into the first bin until the first bin capacity $MAX_{BIN\ 1}$ is reached and refraining from placing subsequent first-type particles in the first bin even if $N_{MAX}$ is not reached; and
   placing the second-type particles into the second bin until the second bin capacity $MAX_{BIN\ 2}$ is reached and refraining from placing subsequent second-type particles in the second bin even if $N_{MAX}$ is not reached.

5. The method of claim 4, wherein each of $MAX_{BIN\ 1}$ and $MAX_{BIN\ 2}$ is less than $N_{MAX}$ but a sum of the $MAX_{BIN\ 1}$ and $MAX_{BIN\ 2}$ is greater than $N_{MAX}$.

6. The method of claim 4 further comprising:
   assigning a first edit weight to the first-type particles, wherein the first edit weight is a correction factor that compensates for a number of first-type particles that are not placed into the first bin; and
   assigning a second edit weight to the second-type particles, wherein the second edit weight is a correction factor that compensates for a number of second-type particles that are not placed into the second bin.

7. The method of claim 6 further comprising determining the concentration of the first class particles by:
   obtaining a sum of the edit weights that are assigned to particles in the first class;
   multiplying the sum with the first class weight to generate a product; and
   dividing the product with Run Equivalency Factor, which is a volume of the sample.

8. The method of claim 4, wherein the bin selection process is performed before the classifying of the N number of particles.

9. The method of claim 4, wherein the bin selection process is performed after the classifying of the N number of particles.

10. The method of claim 3, wherein N=1, and wherein the edit weight for each particle is 1.

11. The method of claim 10, wherein calculating the concentration of particles in the first class comprises:
   multiplying a number of particles in the first class and the first class weight to generate a corrected number of first class particles, and dividing the number of first class particles by a sample volume.

12. The method of claim 1 further comprising:
   reclassifying one of the particles; and
   modifying the first class weight in response to the reclassifying before the multiplying of the number particles classified in the first class by the first class weight.

13. The method of claim 12 further comprising:
   determining an edit weight for each of the particles; and
   calculating a concentration of the first class particles and the second class particles by using the class weights and the edit weights.

14. The method of claim 13, wherein N is less than or equal to I and determining the edit weight comprises a bin selection process that includes:
   setting up a first bin for first-type particles and a second bin for second-type particles, wherein the first-type particles and the second-type particles are defined by a set of mutually exclusive bin selection criteria;

selecting a maximum particle number ($N_{MAX}$) to be checked for placement into the first bin and the second bin;

setting a maximum first bin capacity $MAX_{BIN\ 1}$ for the first bin and a maximum second bin capacity $MAX_{BIN\ 2}$ for the second bin; and placing the first-type particles into the first bin until the first bin capacity $MAX_{BIN\ 1}$ is reached and refraining from placing first-type particles in the first bin after $MAX_{BIN\ 1}$ is reached; and placing the second-type particles into the second bin until the second bin capacity $MAX_{BIN\ 2}$ is reached and refraining from placing second-type particles in the second bin after $MAX_{BIN\ 2}$ is reached.

15. The method of claim 14, wherein each of $MAX_{BIN\ 1}$ and $MAX_{BIN\ 2}$ is less than $N_{MAX}$ but a sum of the $MAX_{BIN\ 1}$ and $MAX_{BIN\ 2}$ is greater than $N_{MAX}$.

16. The method of claim 14 further comprising:

assigning a first edit weight to the first-type particles, wherein the first edit weight is a correction factor that compensates for a number of first-type particles that are not placed into the first bin; and assigning a second edit weight to the second-type particles, wherein the second edit weight is a correction factor that compensates for a number of second-type particles that are not placed into the second bin.

17. The method of claim 14 further comprising determining the concentration of the first class particles by:

obtaining a sum of the edit weights of the first class particles;

multiplying the sum with the modified first class weight to generate a product; and dividing the product with Run Equivalency Factor, which is a volume of the sample.

18. The method of claim 14, wherein the bin selection process is performed before the classifying of the N number of particles.

19. The method of claim 14, wherein the bin selection process is performed after the classifying of the N number of particles.

20. The method of claim 12, wherein N=I, and wherein the edit weight for each particle is 1.

21. The method of claim 20 further comprising determining a concentration of first class particles in the sample by multiplying the number of first class particles and the modified first class weight to generate a corrected number of first class particles, and dividing the number of first class particles by sample volume.

22. The method of claim 12, wherein the reclassification comprises moving a particle from one of the classes to either the first class or the second class.

23. The method of claim 12, wherein modifying the first class weight comprises:

determining the total number of particles ($N_{Moved}$) that are reclassified;

multiplying the value ($N-N_{Moved}$) with the first class weight to generate an intermediate first class weight;

adding the number $N_{Moved}$ to the intermediate first class weight to generate a sum; and dividing the sum with N to generate a modified first class weight.

24. The method of claim 12, wherein modifying the first class weight comprises decreasing the first class weight by:

determining the total number of particles ($N_{Moved}$) that are reclassified;

subtracting ($N_{Moved}$) from a sum of edit weights of the particles that are classified into the first class to generate a difference;

dividing the difference by the sum of edit weights of the particles that are classified into the first class to generate a coefficient;

multiplying the coefficient with the first class weight to generate a product; and setting the first class weight to a greater value between 1 and the product.

25. The method of claim 12, wherein modifying the first class weight comprises increasing the first class weight by:

determining the total number of particles ($N_{Moved}$) that are reclassified;

adding ($N_{Moved}$) to a sum of edit weights of the particles that are classified into the first class to generate a nominator;

dividing the nominator by the sum of edit weights of the particles that are classified into the first class to generate a coefficient; and setting the first class weight to a product of the coefficient and the first class weight.

26. The method of claim 1, wherein the N particles are classified using particle images, further comprising:

obtaining still frames of different portions of the sample; and extracting particle images from the still frames.

27. A computer-readable medium having computer executable instructions thereon for analyzing a sample that contains I particles, said instructions comprising:

instructions for classifying N number of particles into one of a first class, a second class, and an artifact class, wherein the classifying into the first and second classes is performed based upon the particles meeting first and second predefined class criteria, respectively, and wherein the classifying into the artifact class is performed based upon a failure of the particles to meet either of the first and second predefined class criteria;

instructions for determining first and second class weights based upon known prior mis-classifications of particles for the first and second classes;

instructions for multiplying a number of the particles classified into the first class by the first class weight to generate a corrected number of particles classified into the first class; and instructions for multiplying a number of the particles classified into the second class by the second class weight to generate a corrected number of particles classified into the second class.

28. The computer-readable medium of claim 27 further comprising instructions for assigning a class weight of one to particles in the artifact class.

29. The computer-readable medium of claim 27 further comprising:

instructions for determining an edit weight that is associated with each of the particles; and instructions for calculating a concentration of the first class particles and the second class particles by using the class weight and the edit weight.

30. The computer-readable medium of claim 29, wherein N is less than or equal to I and the instructions for determining the edit weight comprises instructions for bin selection including:

instructions for setting up a first bin for first-type particles and a second bin for second-type particles, wherein the first-type particles and the second-type particles are defined by a set of mutually exclusive bin selection criteria;

instructions for selecting a maximum particle number ($N_{MAX}$) to be checked for placement into the first bin and the second bin;

instructions for setting a maximum first bin capacity $MAX_{BIN\ 1}$ for the first bin and a maximum second bin capacity $MAX_{BIN\ 2}$ for the second bin; and instructions for placing the first-type particles into the first bin until the first bin capacity $MAX_{BIN\ 1}$ is reached and refraining from placing subsequent first-type particles in the first bin even if $N_{MAX}$ is not reached; and instructions for placing the second-type particles into the second bin until the second bin capacity $MAX_{BIN\ 2}$ is reached and refraining from placing subsequent second-type particles in the second bin even if $N_{MAX}$ is not reached.

31. The computer-readable medium of claim 30, wherein each of $MAX_{BIN\ 1}$ and $MAX_{BIN\ 2}$ is less than $N_{MAX}$ but a sum of the $MAX_{BIN\ 1}$ and $MAX_{BIN\ 2}$ is greater than $N_{MAX}$.

32. The computer-readable medium of claim 30, further comprising;

instructions for assigning a first edit weight to the first-type particles, wherein the first edit weight is a correction factor that compensates for a number of first-type particles that are not placed into the first bin; and instructions assigning a second edit weight to the second-type particles, wherein the second edit weight is a correction factor that compensates for a number of second-type particles that are not placed into the second bin.

33. The computer-readable medium of claim 32 further comprising instructions for determining the concentration of the first class particles by:

obtaining a sum of the edit weights that are assigned to particles in the first class;

multiplying the sum with the first class weight to generate a product; and dividing the product with a volume of the sample.

34. The computer-readable medium of claim 30, wherein the bin selection process is performed before the classifying of the N number of particles.

35. The computer-readable medium of claim 30, wherein the bin selection process is performed after the classifying of the N number of particles.

36. The computer-readable medium of claim 29, wherein N=I, and wherein the edit weight for each particle is 1.

37. The computer-readable medium of claim 36, wherein the instructions for calculating the concentration of particles in the first class comprises:

instructions for multiplying a number of particles in the first class and the first class weight to generate a corrected number of first class particles, and dividing the number of first class particles by a sample volume.

38. The computer-readable medium of claim 27 further comprising:

instructions for reclassifying one of the particles; and instructions for modifying the first class weight in response to the reclassifying before executing the instructions for multiplying the number of the particles classified into the first class by the first class weight to generate a corrected number of particles classified into the first class.

39. The computer-readable medium of claim 38 further comprising:

instructions for determining an edit weight that is associated with each of the particles; and instructions for calculating a concentration of the first class particles and the second class particles by using the class weights and the edit weights.

40. The computer-readable medium of claim 39, wherein N is less than or equal to I and the instructions for determining the edit weight comprises:

instructions for setting up a first bin for first-type particles and a second bin for second-type particles, wherein the first-type particles and the second-type particles are defined by a set of mutually exclusive bin selection criteria;

instructions for selecting a maximum particle number ($N_{MAX}$) to be checked for placement into the first bin and the second bin;

instructions for setting a maximum first bin capacity $MAX_{BIN\ 1}$ for the first bin and a maximum second bin capacity $MAX_{BIN\ 2}$ for the second bin; and instructions for placing the first-type particles into the first bin until the first bin capacity $MAX_{BIN\ 1}$ is reached and refraining from placing first-type particles in the first bin after $MAX_{BIN\ 1}$ is reached; and instructions for placing the second-type particles into the second bin until the second bin capacity $MAX_{BIN\ 2}$ is reached and refraining from placing second-type particles in the second bin after $MAX_{BIN\ 2}$ is reached.

41. The computer-readable medium of claim 40, wherein each of $MAX_{BIN\ 1}$ and $MAX_{BIN\ 2}$ is less than $N_{MAX}$ but a sum of the $MAX_{BIN\ 1}$ and $MAX_{BIN\ 2}$ is greater than $N_{MAX}$.

42. The computer-readable medium of claim 40 further comprising:

instructions for assigning a first edit weight to the first-type particles, wherein the first edit weight is a correction factor that compensates for a number of first-type particles that are not placed into the first bin; and instructions for assigning a second edit weight to the second-type particles, wherein the second edit weight is a correction factor that compensates for a number of second-type particles that are not placed into the second bin.

43. The computer-readable medium of claim 40 further comprising instructions for determining the concentration of the first class particles by:

obtaining a sum of the edit weights of the first class particles;

multiplying the sum with the modified first class weight to generate a product; and dividing the product with a volume of the sample.

44. The computer-readable medium of claim 40, wherein the bin selection process is performed before the classifying of the N number of particles.

45. The computer-readable medium of claim 40, wherein the bin selection process is performed after the classifying of the N number of particles.

46. The computer-readable medium of claim 38, wherein N=I, and wherein the edit weight for each particle is 1.

47. The computer-readable medium of claim 46 further comprising instructions for determining a concentration of first class particles in the sample by multiplying the number of first class particles and the modified first class weight to generate a corrected number of first class particles, and dividing the number of first class particles by sample volume.

48. The computer-readable medium of claim 38, wherein the reclassification comprises moving a particle from one of the classes to either the first class or the second class.

49. The computer-readable medium of claim 38, wherein the instructions for modifying the first class weight comprises:
- instructions for determining the total number of particles ($N_{Moved}$) that are reclassified;
- instructions for multiplying the value ($N-N_{Moved}$) with the first class weight to generate an intermediate first class weight;
- instructions for adding the number $N_{Moved}$ to the intermediate first class weight to generate a sum; and
- instructions for dividing the sum with N to generate a modified first class weight.

50. The computer-readable medium of claim 38, wherein instructions for modifying the first class weight comprises instructions for decreasing the first class weight by:
- determining the total number of particles ($N_{Moved}$) that are reclassified;
- subtracting ($N_{Moved}$) from a sum of edit weights of the particles that are classified into the first class to generate a difference;
- dividing the difference by the sum of edit weights of the particles that are classified into the first class to generate a coefficient;
- multiplying the coefficient with the first class weight to generate a product; and
- setting the first class weight to a greater value between 1 and the product.

51. The computer-readable medium of claim 38, wherein the instructions for modifying the first class weight comprises instructions for increasing the first class weight by:
- determining the total number of particles ($N_{Moved}$) that are reclassified;
- adding ($N_{Moved}$) to a sum of edit weights of the particles that are classified into the first class to generate a nominator;
- dividing the nominator by the sum of edit weights of the particles that are classified into the first class to generate a coefficient; and
- setting the first class weight to a product of the coefficient and the first class weight.

52. The computer-readable medium of claim 27, wherein the N particles are classified using particle images, further comprising:
- instructions for obtaining still frames of different portions of the sample; and
- instructions for extracting particle images from the still frames.

53. A computer-readable medium having computer executable instructions thereon for analyzing a fluid sample, said instructions comprising:
- instructions for classifying N number of particles into one of a first class, a second class, and an artifact class, wherein the classifying into the first and second classes is performed based upon the particles meeting first and second predefined class criteria, respectively, and wherein the classifying into the artifact class is performed based upon a failure of the particles to meet either of the first and second predefined class criteria;
- instructions for determining first and second class weights based upon known prior mis-classifications of particles for the first and second classes;
- instructions for multiplying a number of the particles classified into the first class by the first class weight to generate a corrected number of particles classified into the first class; and
- instructions for multiplying a number of the particles classified into the second class by the second class weight to generate a corrected number of particles classified into the second class.

* * * * *